(12) United States Patent
Feng

(10) Patent No.: US 6,170,484 B1
(45) Date of Patent: Jan. 9, 2001

(54) FEMALE CONTRACEPTIVE DEVICE

(76) Inventor: Du Xiong Feng, 12705 Roark Ct., Herndon, VA (US) 20191

(*) Notice: Under 35 U.S.C. 154(b), the term of this patent shall be extended for 0 days.

(21) Appl. No.: 09/522,624

(22) Filed: Mar. 10, 2000

(51) Int. Cl.$^7$ .................................................. A61F 6/06
(52) U.S. Cl. .................................... 128/830; 128/834
(58) Field of Search ................................. 128/830–841

(56) References Cited

U.S. PATENT DOCUMENTS

| | | | |
|---|---|---|---|
| 435,491 | * 9/1890 | Fredigke | 128/834 |
| 2,613,670 | * 10/1952 | Sokojik | 128/834 |
| 3,683,904 | * 8/1972 | Forster | 128/834 |
| 3,811,423 | * 5/1974 | Dickinson | 128/830 |

* cited by examiner

*Primary Examiner*—Michael A. Brown
(74) *Attorney, Agent, or Firm*—Oblon, Spivak, McClelland, Maier & Neustadt, P.C.

(57) ABSTRACT

An approach for providing a female contraceptive device is disclosed. The contraceptive device has an upper portion that contacts the cervix and an outer wall. A lower portion of the contraceptive device has corrugated inner walls that form a hollow petal-shaped sections with the outer wall. Each of the petal-shaped sections has a curled edge and is capable of storing semen. The inner wall of the lower portion forms a cavity that receives the penis. The outer wall of the lower portion has surface protrusions that creates a barrier to the flow of semen, yet permits the flow of vaginal secretion. The contraceptive device occupies the upper portion of the vaginal canal, leaving the lower portion of the canal exposed to enhance sensitivity. The bulbous shape of the contraceptive device provides additional sensual stimulation for the female, while the corrugated inner walls enhance simulation for the male.

20 Claims, 6 Drawing Sheets

FEMALE CONTRACEPTIVE DEVICE

BACKGROUND OF THE INVENTION

1. Field of the Invention

The present invention relates to reproductive health, and is more particularly related to a female contraceptive device.

2. Discussion of the Background

Because modem society faces the challenge of controlling the spread of sexually transmitted disease and overpopulation, development of effective contraceptive measures are vital to addressing these issues. Accordingly, numerous approaches have emerged: the pill, male condom, and various female contraceptive devices (e.g., IUDs (intrauterine devices), diaphragms, and female condoms).

The traditional pill provides a relatively high level of prevention against pregnancy. However, a number of drawbacks attend such a solution. Most significantly, the pill can produce unwanted side effects, such as hormonal disturbance and migraine headaches. Also, the pill does not assist with the prevention of sexually transmitted diseases. Further, administration of the pill requires the assistance of a physician and, therefore, lacks convenience.

The conventional male condom reduces the transmission of diseases, but is not nearly as successful at preventing conception. The relatively poor success rate stems from the fact that the condoms can rupture or, more often than not, are incorrectly used. In addition, couples are sometimes reluctant to use condoms because the male partner experiences reduced or dulling of sexual sensation.

Consequently, research and development has also focused on female contraceptive devices. One such female contraceptive device is the intrauterine device (IUD), which is inserted into the uterus. As such, an IUD is an inconvenient alternative, in that a physician is required properly insert the device. Significantly, the harmful side effects of IUDs are well known.

Additionally, diaphragms have been used to prevent pregnancy. To be effective, the diaphragm must be fitted for the individual female, thus requiring the help of the physician, who also inserts the device. Therefore, accessibility of this contraceptive device is low; namely, users view doctor visitations has highly inconvenient. In addition to being inconvenient, diaphragms are relatively ineffective against unwanted pregnancies.

Another female contraceptive device is the vaginal cover (or female condom), which covers a large amount of the sensitive areas of the vagina. The vaginal cover is a soft membrane blind tube, in which the open end extends and connects to a side ring. Another ring in attached to the other end. The blind tube seals the entirety of the vaginal cavity to block semen from entering the uterus. However, the artificial membrane covers the sexually sensitive areas of the female, thus negatively affecting sexual stimulation and sexual psychological well-being of the female. The female may feel undue anxiety from the fact that the female condom is visibly noticeable. The device is not easily applied, as the device needs to be led in by bottom ring and clamped to the upper side of vaginal cavity. The sexual response is also diminished for the male partner. As applied, the device is aesthetically displeasing.

Based on the foregoing, there is a clear need for improved approaches to raising contraceptive effectiveness.

There is also a need to prevent and reduce sexually transmitted diseases.

There is also a need to permit case of application of the contraceptive device.

There is also a need to develop a contraceptive device that is readily accessible.

There is a further need to enhance sexual stimulation for both the male and female partners.

Based on the need to improve effectiveness of the female contraceptive device, an approach for preventing pregnancies and diseases while promoting sexual stimulation is highly desirable.

SUMMARY OF THE INVENTION

According to one aspect of the invention, a contraceptive device comprises an upper portion for providing cervical contact. An outer wall has surface protrusions. A lower portion has a plurality of corrugated inner walls that form a plurality of hollow petal-shaped sections with the outer wall. Each of the hollow petal-shaped sections has a curled edge and stores fluid; the hollow petal-shaped sections form a cavity. Under this approach, a female can easily apply the contraceptive device without the aid of a physician.

According to another aspect of the invention, an contraceptive device having a bulbous shape comprises a plurality of petal-shaped sections. Each of the petal-shaped sections has a corrugated inner side. Each of the petal-shaped sections has a curled edge and stores fluid; the plurality of petal-shaped sections form a cavity. A cervical contact side is opposite to the petal-shaped sections. An outer wall has a patterned surface protrusions, which provide a barrier for unidirectional fluid flow. The above arrangement advantageously provides enhanced sexual stimulation for the female and male, while preventing unwanted pregnancies.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

In the following description, for the purpose of explanation, specific details are set forth in order to provide a thorough understanding of the invention. However, it will be apparent that the invention may be practiced without these specific details.

The present invention provides an effective approach to female contraception by exhibiting a high rate of prevention against pregnancy and disease, while providing increased stimulation for the male and female partners. The contraceptive device has an upper portion that contacts the cervix. A lower portion of the contraceptive device has a corrugated inner wall and an outer wall, which form a plurality of hollow petal-shaped sections. Each of the petal-shaped sections is capable of storing semen. The inner wall of the lower portion forms a cavity that receives the penis, which is stimulated by the corrugation on the inner wall. The outer wall of the lower portion has surface protrusions that create a barrier to the flow of semen, yet permits the flow of vaginal secretion. The contraceptive device occupies the lower vaginal canal, leaving the upper canal exposed to enhance sensitivity. The bulbous shape of the contraceptive device provides additional sensual stimulation for the female.

Figure 1:
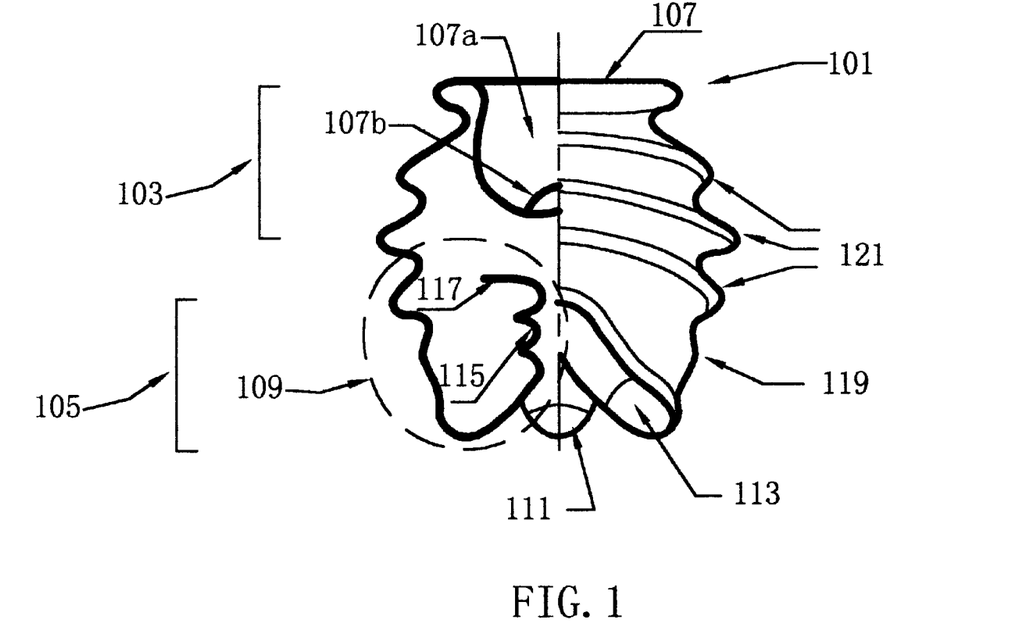
FIG. 1 is a semi-sectional drawing of the contraceptive device according to one embodiment of the present invention.

FIG. 1 shows a semi-sectional drawing of the contraceptive device according to one embodiment of the present invention. The female contraceptive device 101, as shown, has a bulbous shape with an upper portion 103 and a lower portion 105. The device 101, according to one embodiment, is made of durable, soft, elastic material, such as latex. In the upper portion 103, a cervical contact side 107 is concave, forming in a bowl-like cavity 107a. At the center of the bowl-like cavity 107a is a reversed hollow navel 107b. The lower portion 105 of the device 101 has multiple petal-shaped sections 109, 111, and 113, which in this embodiment total three. Each of these petal-shaped sections 109, 111, and 113 has a corrugated inner wall 115. According to one embodiment, the corrugation is tripe-like in texture. As will be explained below in FIG. 4, this corrugated inner wall 115 promotes sexual sensation for the male partner. The petal-shaped sections 109, 111, and 113 constitute a cavity (or hollow tube) that receives a penis. These petal-shaped sections 109, 111, and 113 are hollow sacs, which store semen. The semen is prevented from flowing back into the cavity (and ultimately to the vaginal canal), in part, by the curled edge 117 of the inner wall 115. The curled edge 116 enhances the ability of the device 101 to retain semen, thereby increasing contraceptive effectiveness. In an exemplary embodiment, the tops of the petal-shaped sections 109, 111, and 113 are cuspidal. The outer wall 119 of the device 101 has surface protrusions 121, which according to one embodiment form a double-layer wavy ring-shaped pattern. These surface protrusions 121, as will be more fully discussed with respect to FIG. 3, control the flow of bodily fluids (e.g., vaginal fluid and semen).

The physical dimensions of the device 101 can vary according to the anatomical characteristics of the female. According to one embodiment, the cervical contact side 107 has a diameter of about 1.50 inches. The height of the device 101 is about 2.25 inches from the cervical contact side 107 to the tip of a petal-shaped section 109. The middle portion of the device 101 has a diameter of about 2.00 inches.

Figure 2:
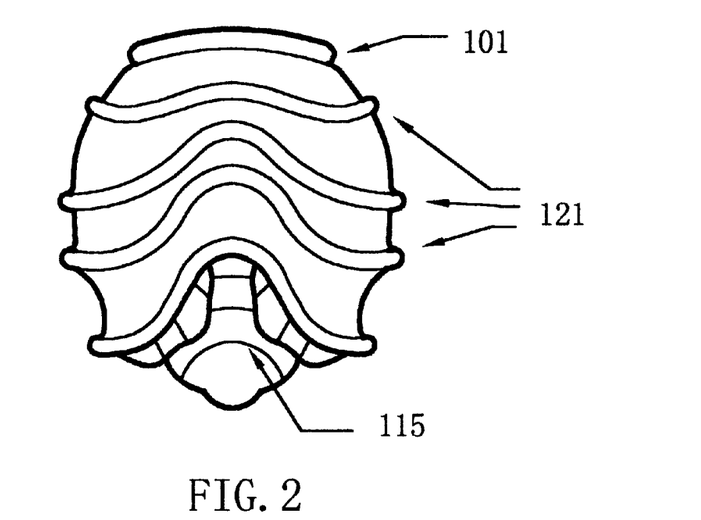
FIG. 2 is a diagram showing the contraceptive device with surface protrusions of double-layer walls and three petal-shaped sections, according to the contraceptive device of FIG. 1.

FIG. 2 shows a side view of the female contraceptive device 101. As seen in the figure, the surface protrusions 121 curve in a wavy ring-shaped pattern, providing a double-layered outer wall 119. The corrugated inner wall 115 is also shown. The operation of the device 101 is described below.

Figure 3:
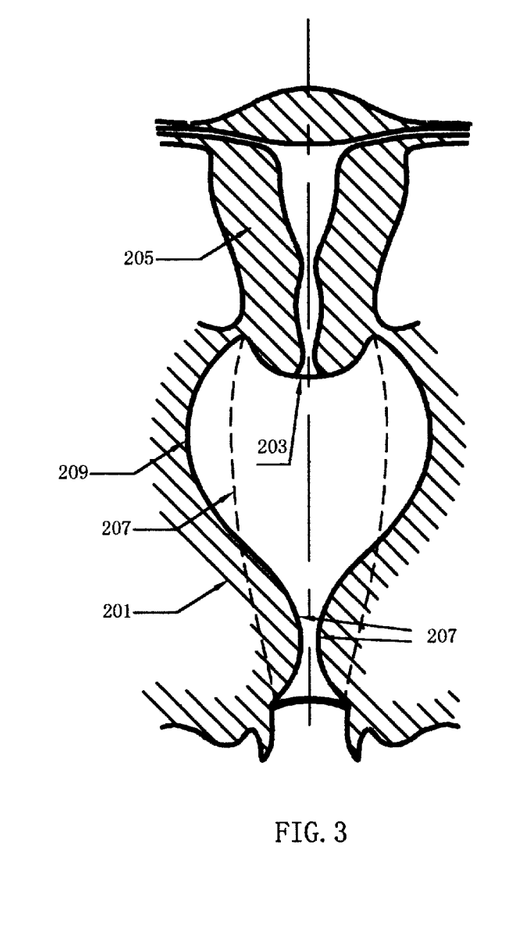
FIG. 3 is a diagram showing the vaginal canal during two physiological states.

FIG. 3 illustrates two states of the vaginal canal. The parts of the female reproductive organs that are directly pertinent to the operation of the female contraceptive device 101 according to various embodiments of the present invention include the vaginal canal 201, the cervix 203, and the uterus 205. Based upon the theory of female anatomy, sexual physiology and psychology, the two states of the vaginal canal 201 involves a non-constricted state and a constricted state. The vaginal canal 201 is essentially is a muscular tube, in which the upper portion, is wider than the lower portion, with the front wall pressing close to the rear wall. As a muscle, the vaginal canal has good extension capacity. Dashed lines 207 denote the non-constricted state; the contraceptive device 101 is inserted during this state.

Figure 4:
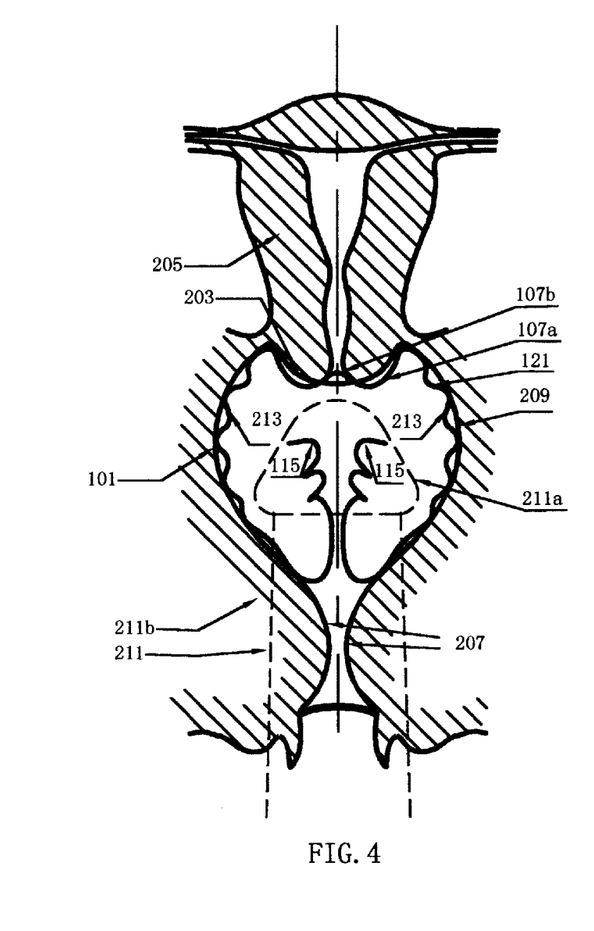
FIG. 4 is a diagram showing the placement of the contraceptive device within the vaginal canal.

The female inserts the contraceptive device 101 by folding the device 101 along the vertical axis during the non-constricted state. Because the device 101 is made of a soft material, the device 101 can be rolled into a thin stick and easily inserted; the device 101, once inserted, automatically decompresses in place. As necessary, lubrication is applied to the contraceptive device 101 before insertion in the vaginal canal 201. The user inserts until the cervical contact side 107 abuts the cervix 203 (as shown in FIG. 4). The female can perform this insertion process without the assistance of a physician. During the non-constricted state, the contraceptive device is compressed by the vaginal canal walls.

However, during sexual excitement, the vaginal canal 201 transitions to a constricted state. The narrow lower portion 207, which constitutes about ⅓ of the vaginal canal, constricts, and the upper portion 209 (about ⅔ of the vaginal canal 201) fully extends as a result of the uterus 205 raising upward. In the constricted state, the upper portion 209 forms a spherical cavity of about 6.5 cm in diameter, while the lower portion 207 constricts. Because the contraceptive device 101 is placed in the upper portion 209, the device 101 expands from its compressed configuration to fulfill the upper portion 209. The positioning of the device 101 leaves the lower portion 207 of the vaginal canal 201 to exposed. Because the lower portion 207 of vaginal canal 201 is highly sensitive, especially in the front wall (not shown), the female experiences strong sexual stimulation.

The device 101 also provides stimulation for the upper portion 209 of the vaginal canal 201 (i.e., tactile sensation). Although fewer nerves exist in the upper portion 209, sexual intensity can be greater if properly stimulated. The device 101 provides proper to stimulation by filling the tipper portion 209 of the vaginal canal 201.

As seen in FIG. 4, the female contraceptive device 101 rests in the upper portion 209, whereby the hollow navel 107b is situated at the opening of the cervix 203. The bowl like cavity 107a surrounds the cervix 203 to anchor the device 101; that is, this configuration helps secure the device 101 so that the cervical open remains covered. As the female experiences sexual stimulation, vaginal secretion flows from the upper portion 209 of the vaginal canal 201 down to the lower portion 207. The device 101 does not impede this flow, because the surface protrusions 121 promote fluid progression in the downward direction. That is, the surface protrusions 121 provide a unidirectional flow of fluids from the upper portion 209 of the vaginal canal 201 to the lower portion 207.

During copulation, the head 211a of the penis 211 enters the cavity formed by the petal-shaped sections 109, 111, and 113. These petal-shaped sections 109, 111, and 113 constrict the head 211a and part of the shaft 211b, thereby enhancing the sensation for the male partner. Additionally, the corrugated inner walls 115 supply extra frictional contact to stimulate the head 211a, which is the most sensitive part of the penis 211. The reversed hollow navel 107b can receive the tip of the head 211a. Upon ejaculation, the semen contacts the bottom side of the hollow navel 107b, which diverts the fluid down the sides 213. The semen is then trapped in the hollow sacs of the petal-shaped sections 109, 111, and 113. After completion of sexual activity, the female can easily remove the device 101 by reaching in the vaginal canal 201 and grasping hold of one of the petal-like sections 109, 111, and 113, gently guiding the device 101 out the vaginal opening.

The obstruction of sperm from entering the cervix 203 is desired for the purposes of contraception and prevention of venereal diseases. Exposure of the cervix 203 to foreign particles or fluid carrying bacteria is a common source of disease; accordingly, blockage of the cervical opening provides an effective method to disease prevention. For instance, by covering the cervix 203 from semen, the device 101 prevents females effectively from carcinogenesis that can be caused from dirt in the prepuce of the penis 211 entering the cervix 203. The device 101 achieves successful blockage by fully sealing the cervix 203 and providing an expansion area to fill and seal the spherical cavity of the upper portion 209 of the vaginal canal 201. The device 101 stores the ejaculated sperm securely within the hollow sacs of the petal-shaped sections 109, 111, and 113. The hollow sacs operate on a similar principle as a one-way valve, as found in the heart, such that the sacs self-close. The surface protrusions 121 are designed to provide essentially unidirectional flow of fluids; therefore, any residual semen not captured within the hollow sacs is impeded from traveling up along the sides of the upper portion 209 of the vaginal canal 201 towards the cervix 203.

Figure 5:
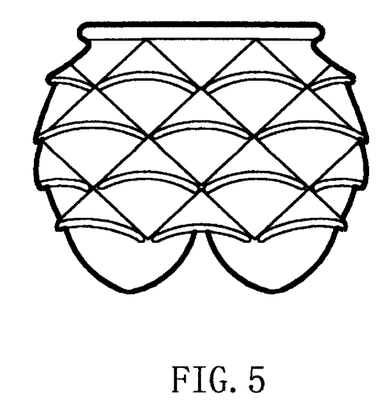
FIG. 5 is a diagram showing the contraceptive device with surface protrusions that follow a scale-and-shell pattern, according to one embodiment of the present invention.
Figure 6:
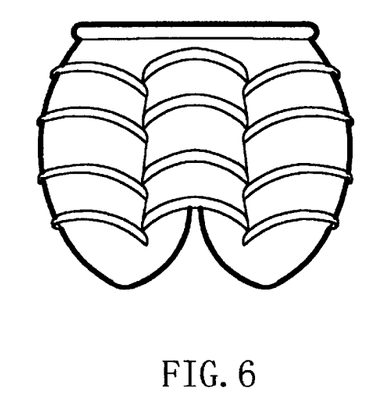
FIG. 6 is a diagram showing the contraceptive device with surface protrusions that follow an arc-tile pattern, according to one embodiment of the present invention.
Figure 7:
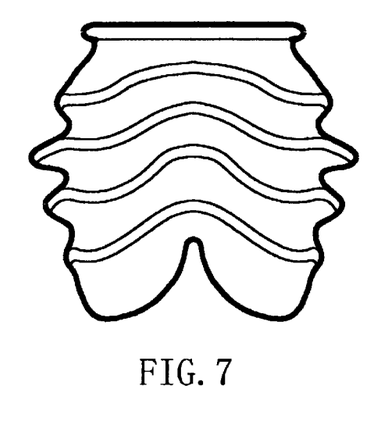
FIG. 7 is a diagram showing the contraceptive device with surface protrusions that follow wavy ring-shaped pattern, according to one embodiment of the present invention.
Figure 8:
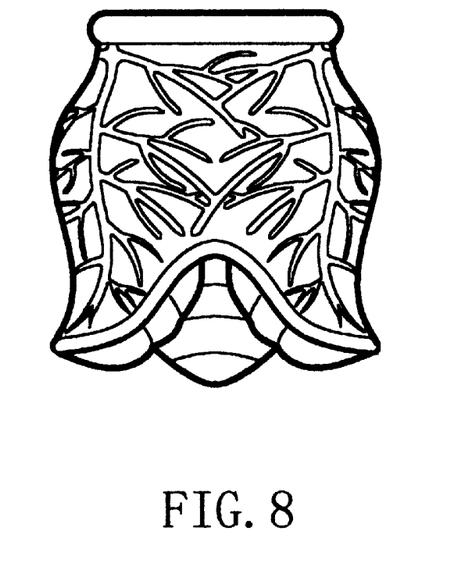
FIG. 8 is a diagram showing the contraceptive device with surface protrusions that follow a branching pattern, according to one embodiment of the present invention.
Figure 9:
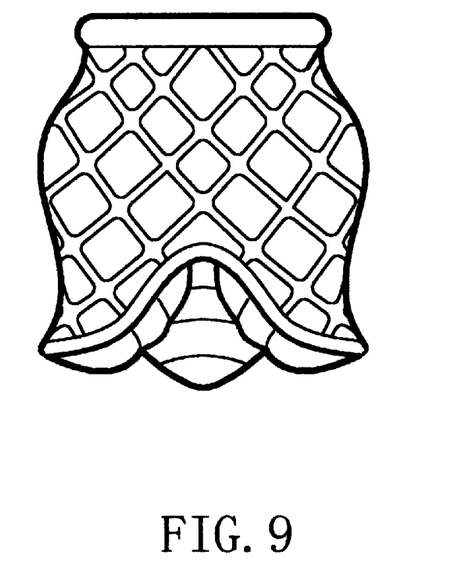
FIG. 9 is a diagram showing the contraceptive device with surface protrusions that follow a diamond-shaped pattern, according to one embodiment of the present invention.

These surface protrusions can follow any number of other patterns (as shown in FIGS. 5–9). FIG. 5 illustrates surface protrusions 121 in a scale-and-shell pattern. The surface protrusions 121 may also follow an arc-tile pattern, as in FIG. 6. FIG. 7 shows the device 101 With surface protrusions 121 in a wavy ring-shaped pattern (similar to FIG. 2). FIG. 8 shows surface protrusions 121 in a branching pattern (or foliage-like). In yet another embodiment, as shown in FIG. 9, the surface protrusions 121 exhibit a diamond-shaped pattern. The surface protrusions 121, as mentioned above, direct flow of fluids as well as contribute to the ease of compression of the device 101 for insertion into the vaginal canal 207.

Figure 10:
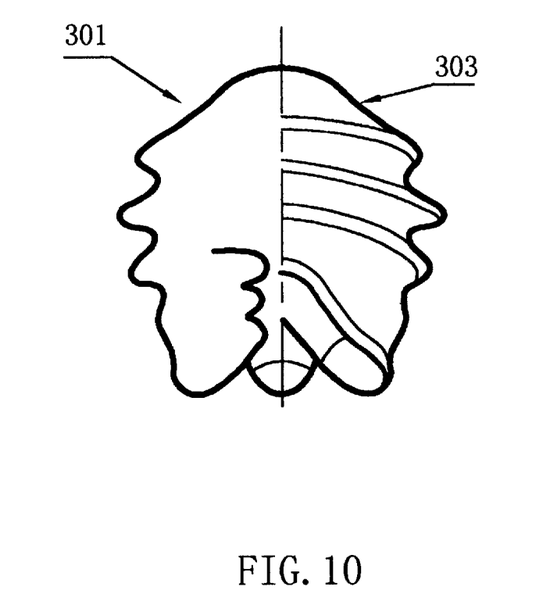
FIG. 10 is a semi-sectional drawing of the contraceptive device with a convex upper portion, according to one embodiment of the present invention.
Figure 11:
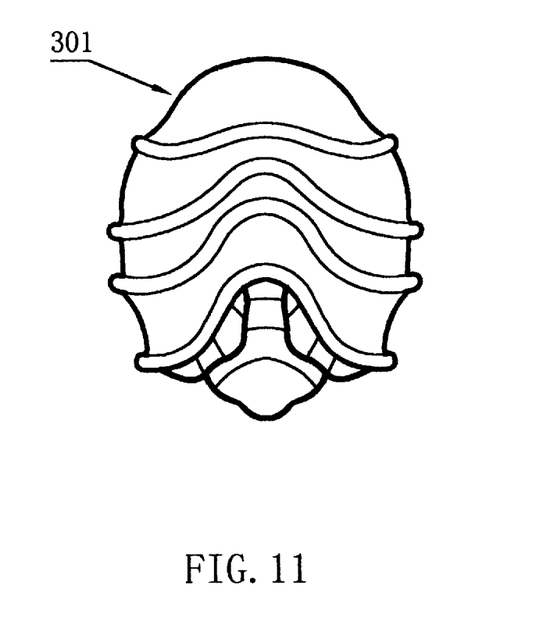
FIG. 11 is a diagram showing the contraceptive device with surface protrusions of double-layer walls and three petal-shaped sections in the contraceptive device of FIG. 10.

FIGS. 10 and 11 shows an embodiment of the present invention in which the contraceptive device has a convex cervical contact side. The female contraceptive device 301 operates in similar fashion to the contraceptive device of FIGS. 1–2. The convex cervical contact side 303 reduces manufacturing complexity. Accordingly, the device 301 can be produced more economically that the embodiment of FIG. 1. Because the device 303 is elastic, the convex cervical contact 303 is dented inwards upon contact with the cervix 203. In an exemplary embodiment, the device 303 can more readily be produced as a disposable device, with the convenience of the male condom, for instance.

Figure 12:
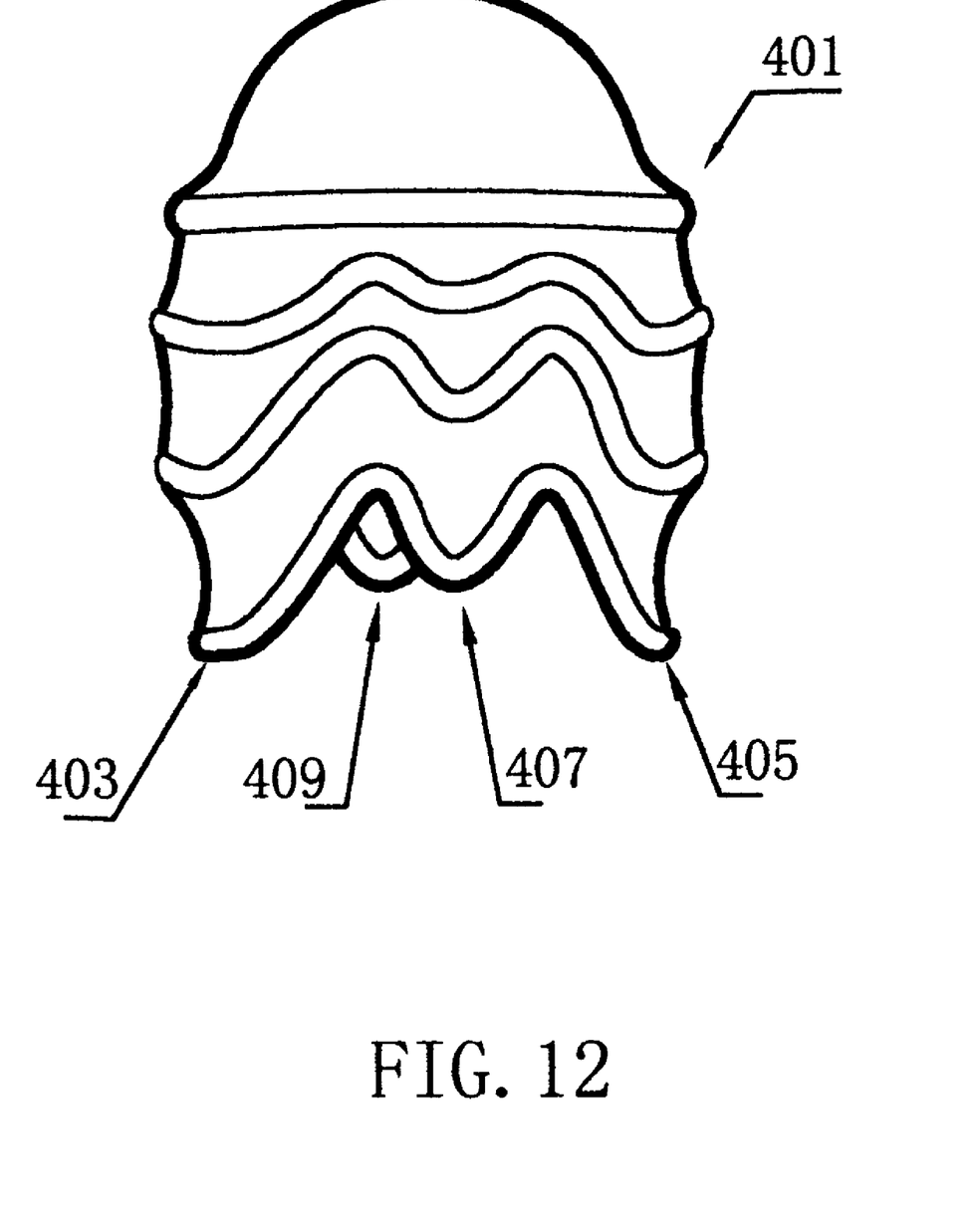
FIG. 12 is a drawing of the contraceptive device with four petal-shaped sections, according to one embodiment of the present invention.

FIG. 12 shows a contraceptive device with a convex cervical contact side and four petal-shaped sections, in accordance with an embodiment of the present invention. Although four petal-shaped sections 403, 405, 407, and 409 are shown, it is understood that any number of petal-shaped sections can be employed (e.g., 2). As shown in this figure, the petal-shaped sections 403 and 405, which are opposite each other, are more cuspidal in shape than the petal-shaped sections 407 and 409. Additionally, petal-shaped sections 407 and 409 are shorter in length than petal-shaped sections 403 and 405. The different lengths of the petal-shaped sections provide greater clamping or constriction of the penis 211, thereby increasing stimulation for the male. The exact design of the device 401 with respect to the number of petals and protrusion surface patterns can be tailored to the individual female. As to the number and shape of petal-shaped sections as well as the surface protrusion patterns, these parameters can be selected depending, on different individuals and their anatomical characteristics. For instance, a greater circumference of the device 401 can be obtained by increasing the number of petal-shaped sections. Manufacturers can thus provide these female contraceptive devices in a variety of configurations, so that the users can experiment for themselves the design best suited to their needs.

The female contraceptive device described herein provides several advantages over prior approaches to contraception and disease prevention. One advantage is the reduction of sexually transmitted diseases. The device also advantageously provides improved contraceptive effectiveness. Additionally because of the convenience of the contraceptive device, implementation of birth control measures can be rapidly deployed. Importantly, sexual stimulation is enhanced for both the female and male partners, thus increasingly the likelihood that contraception will be used.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A contraceptive device comprising:
   an upper portion for providing cervical contact;
   an outer stall having surface protrusions; and
   a lower portion having a plurality of corrugated inner walls that form a plurality of hollow petal-shaped sections with the outer wall, each of the hollow petal-shaped sections having a curled edge and being configured to store fluid, the hollow petal-shaped sections forming a cavity.

2. The device according to claim 1, wherein the upper portion has a convex side.

3. The device according to claim 1, wherein the upper portion has a concave side.

4. The device according to claim 1, wherein each of the inner walls has tripe-like corrugation.

5. The device according to claim 1, wherein the surface protrusions follow a scale-and-shell pattern.

6. The device according to claim 1, wherein the surface protrusions follow an arc-tile pattern.

7. The device according to claim 1, wherein the surface protrusions follow a wavy ring-shaped pattern.

8. The device according to claim 1, wherein the surface protrusions follow a diamond-shaped pattern.

9. The device according to claim 1, wherein the surface protrusions follow a branching pattern.

10. The device according to claim 1, wherein quantity of the plurality of petal-shaped sections is two, three, or four.

11. The device according to claim 1, wherein at least two of the petal-shaped sections are of different lengths.

12. A contraceptive device having a bulbous shape, comprising:
   a plurality of petal-shaped sections, each of the petal-shaped sections having a corrugated inner wall, each of the petal-shaped sections having a curled edge and being configured to store fluid, the plurality of petal-shaped sections forming a cavity;
   a cervical contact side opposite to the petal-shaped sections; and
   an outer wall having patterned surface protrusions for providing a barrier for unidirectional fluid flow.

13. The device according to claim 12, wherein the cervical contact side is convex.

14. The device according to claim 12, wherein the cervical contact side is concave and has a reversed hollow navel.

15. The device according to claim 12, wherein the inner wall has tripe corrugation.

16. The device according to claim 12, wherein the patterned surface protrusions follow a scale-and-shell pattern.

17. The device according to claim 12, wherein the patterned surface protrusions follow a arc-tile pattern.

18. The device according to claim 12, wherein the patterned surface protrusions follow a wavy ring-shaped pattern.

19. The device according to claim 12, wherein the patterned surface protrusions follow a diamond-shaped pattern.

20. The device according to claim 12, wherein the patterned surface protrusions follow a branching pattern.

* * * * *